(12) United States Patent
Liu et al.

(10) Patent No.: US 11,154,090 B2
(45) Date of Patent: Oct. 26, 2021

(54) ULTRASONIC ELECTRONIC CIGARETTE ATOMIZATION CORE AND ATOMIZER

(71) Applicant: CHINA TOBACCO HUNAN INDUSTRIAL CO., LTD., Hunan (CN)

(72) Inventors: Jianfu Liu, Hunan (CN); Kejun Zhong, Hunan (CN); Xiaoyi Guo, Hunan (CN); Wei Huang, Hunan (CN); Hong Yu, Hunan (CN); Yuangang Dai, Hunan (CN); Xinqiang Yin, Hunan (CN); Jianhua Yi, Hunan (CN); Yongquan Zhou, Hunan (CN)

(73) Assignee: CHINA TOBACCO HUNAN INDUSTRIAL CO., LTD., Hunan (CN)

( * ) Notice: Subject to any disclaimer, the term of this patent is extended or adjusted under 35 U.S.C. 154(b) by 272 days.

(21) Appl. No.: 16/337,255

(22) PCT Filed: Feb. 16, 2017

(86) PCT No.: PCT/CN2017/073782
§ 371 (c)(1),
(2) Date: Mar. 27, 2019

(87) PCT Pub. No.: WO2018/058884
PCT Pub. Date: Apr. 5, 2018

(65) Prior Publication Data
US 2019/0230991 A1     Aug. 1, 2019

(30) Foreign Application Priority Data

Sep. 28, 2016 (CN) .......................... 201621087266.5

(51) Int. Cl.
*A24F 40/30* (2020.01)
*A24F 40/05* (2020.01)
(Continued)

(52) U.S. Cl.
CPC .............. *A24F 40/30* (2020.01); *A24F 40/05* (2020.01); *A24F 40/485* (2020.01);
(Continued)

(58) Field of Classification Search
CPC ...... A24F 47/008; A24F 47/00; A24F 47/002; A24F 40/05; A24F 40/20; B05B 17/06; B05B 17/0607
See application file for complete search history.

(56) References Cited

U.S. PATENT DOCUMENTS 6,196,218 B1 * 3/2001 Voges ................. B05B 17/0607
128/200.14
2016/0338407 A1 * 11/2016 Kerdemelidis ......... A24F 40/30
(Continued)

FOREIGN PATENT DOCUMENTS

JP    2008104966 A * 5/2008 ........ A61M 15/0085

OTHER PUBLICATIONS

International Search Report, International Application No. PCT/CN2017/073782, dated Jun. 28, 2017, 4 pages.

*Primary Examiner* — Alex B Efta
(74) *Attorney, Agent, or Firm* — Mauriel Kapouytian Woods LLP; Liang Huang; Michael Mauriel

(57) ABSTRACT

Disclosed are an ultrasonic electronic cigarette atomization core and atomizer, the electronic cigarette atomization core including an atomization core fixing sleeve. A first atomization sheet, a first tobacco tar guide component and a bracket are arranged in the atomization core fixing sleeve. The ultrasonic electronic cigarette atomization core not only can atomize two kinds of tobacco tar at the same time, but also can atomize the solid tobacco product, and the amount of smoke is large, therefore the demands of smokers for different tastes, in particular the demands for the taste of true cigarette, can be satisfied.

12 Claims, 18 Drawing Sheets

(51) Int. Cl.
*A24F 40/485* (2020.01)
*A24F 40/20* (2020.01)
*A61M 15/00* (2006.01)

(52) U.S. Cl.
CPC ......... *A61M 15/0085* (2013.01); *A24F 40/20* (2020.01); *A61M 2205/8206* (2013.01)

(56) References Cited

U.S. PATENT DOCUMENTS

2017/0119040 A1* 5/2017 Cameron ............... A61K 47/10
2017/0280771 A1* 10/2017 Courbat .............. B05B 17/0669

* cited by examiner

ULTRASONIC ELECTRONIC CIGARETTE ATOMIZATION CORE AND ATOMIZER

CROSS REFERENCE TO RELATED APPLICATIONS

This application is a national phase application of international application number PCT/CN2017/073782 filed on Feb. 16, 2017, which claims priority to Chinese application number 201621087266.5 filed on Sep. 28, 2016. The entire contents of these applications are hereby incorporated herein by reference.

TECHNICAL FIELD

The utility model belongs to the technical field of electronic cigarettes, and particularly relates to an ultrasonic electronic cigarette atomization core and atomizer.

BACKGROUND ART

At present, an electronic cigarette has become a relatively mature smoking alternative on the market. Compared with the traditional heating atomization by an electric heating wire, an ultrasonic electronic cigarette atomizes tobacco tar by using an ultrasonic vibration atomization sheet, the atomization temperature is lower, and the atomization temperature does not exceed 180 degrees Celsius, therefore the problem of producing formaldehyde, carbon monoxide and other harmful substances at high temperatures is effectively solved, meanwhile, no peculiar smell will be produced due to scorching at a high temperature, and thus the atomization taste is effectively improved.

The existing ultrasonic electronic cigarette atomization core comprises an atomization core fixing sleeve, wherein an atomization sheet, a tobacco tar guide component and a bracket used for erecting and fixing the atomization sheet are arranged in the atomization core fixing sleeve. Although the atomization sheet essentially comprises a front surface and a back surface (i.e., a first surface and a second surface) that can atomize the tobacco tar, actually the tobacco tar guide component is only in contact with one surface of the atomization sheet, therefore the amount of smoke is relatively small, only one kind of tobacco tar can be atomized at a time, accordingly the taste of smoke is single, and the requirements for multiple tastes cannot be satisfied.

CONTENTS OF INVENTION

The existing ultrasonic electronic cigarette atomization core is only provided with a single-face atomization type atomization sheet, therefore the amount of smoke is small, and only one kind of tobacco tar can be atomized at a time, accordingly the taste of smoke is single. The objective of the utility model is to provide an improved ultrasonic electronic cigarette atomization core and atomizer in view of the shortcomings of the above prior art, in which the amount of smoke is large, and two kinds of tobacco tar can be atomized at the same time.

In order to solve the above-mentioned technical problems, the technical solution adopted by the utility model is as follows:

An ultrasonic electronic cigarette atomization core comprises an atomization core fixing sleeve, wherein a first atomization sheet, a first tobacco tar guide component and a bracket are arranged in the atomization core fixing sleeve, the first atomization sheet comprises a first surface and a second surface, the first atomization sheet is fixed on the bracket, and the first tobacco tar guide component props against the first surface; a second atomization sheet and a second tobacco tar guide component are further arranged in the atomization core fixing sleeve, the second atomization sheet comprises a third surface and a fourth surface, the second atomization sheet is fixed on the bracket, and the second tobacco tar guide component props against the fourth surface; both a first gas pass hole and a second gas pass hole are formed in the bracket and are communicated with the outside, both of the first gas pass hole and the second gas pass hole are communicated with the first surface, and both of the first gas pass hole and the second gas pass hole are communicated with the fourth surface.

By means of the above structure, the first tobacco tar guide component guides the tobacco tar to the first surface of the first atomization sheet for atomization, and the second tobacco tar guide component guides the tobacco tar to the fourth surface of the second atomization sheet for atomization, therefore the first surface and the fourth surface can be used for atomizing the tobacco tar at the same time, and thus the amount of smoke is large. If the first surface and the fourth surface are respectively used for atomizing tobacco tar with different tastes, the requirements of a smoker for different tastes can also be satisfied.

Further, the second surface and the third surface are arranged oppositely, and a solid tobacco product is clamped between the second surface and the third surface; and both of the first gas pass hole and the second gas pass hole are communicated with the solid tobacco product.

By means of the above structure, the solid tobacco product (cut tobacco, tobacco paste, flavor cigarette) is arranged between the first atomization sheet and the second atomization sheet and is in contact with the first atomization sheet and the second atomization sheet, when the atomization core works, the first surface and the fourth surface atomize the tobacco tar to generate smoke, meanwhile the solid tobacco product will absorb the heat on the second surface and the third surface and produce the smoke and flavor of true cigarette, then the smoke and flavor are mixed with the smoke produced by the tobacco tar to realize the taste of the true cigarette at last and increase the amount of smoke, and thus the user experience is improved.

As a preferred implementation, the first tobacco tar guide component comprises tobacco tar guide cotton, a fixing ring, tobacco tar storage cotton and a tobacco tar control cover, the tobacco tar guide cotton is a U-shaped structure which is formed by two opposite side walls and atomization cotton, the two side walls of the tobacco tar guide cotton penetrate through the fixing ring and are in contact with one side face of the tobacco tar storage cotton, and the other side face of the tobacco tar storage cotton is in contact with one side of the tobacco tar control cover; and one side of the atomization cotton is in contact with the first surface.

By means of the above structure, the tobacco tar enters the tobacco tar storage cotton from the tobacco tar control cover, and then is guided to the two side walls of the tobacco tar guide cotton from the tobacco tar storage cotton, and then is guided to the atomization cotton by the two side walls of the tobacco tar guide cotton so as to be atomized by the first atomization sheet. The first tobacco tar guide component can be replaced if it has been used for a relatively long time, so that it is cleaner, and the taste of the tobacco tar is purer.

As a preferred implementation, the structure of the second tobacco tar guide component is the same as that of the first tobacco tar guide component.

Based on the same inventive concept, the utility model further provides an ultrasonic electronic cigarette atomizer, comprising a tobacco tar cup and a suction nozzle connected with one end of the side wall of the tobacco tar cup, the ultrasonic electronic cigarette atomization core is arranged in the tobacco tar cup, a division plate is arranged in the tobacco tar cup, and a branch pipe is arranged in the side wall of the division plate; the division plate and the atomization core divide the tobacco tar cup into a first tobacco tar bin and a second tobacco tar bin which are not communicated with each other, the first tobacco tar bin is communicated with the first surface through the first tobacco tar guide component, and the second tobacco tar bin is communicated with the fourth surface through the second tobacco tar guide component; and a smoke mixing pipe is arranged in the branch pipe, and the second gas pass hole is communicated with the suction nozzle through the smoke mixing pipe.

According to different demands of the user, tobacco tar with different tastes and concentrations can be stored in the first tobacco tar bin and the second tobacco tar bin, the first tobacco tar guide component and the second tobacco tar guide component respectively guide the tobacco tar in the corresponding tobacco tar bins to the surfaces of the corresponding atomization sheets for atomization, meanwhile the solid tobacco product absorbs the heat to produce the smoke and flavor of the true cigarette, three kinds of smoke are mixed in the smoke mixing pipe to be inhaled by the user, the amount of smoke is large, the taste of smoke is good, the user experience of the smoke taste is improved, and the demands of mixing a plurality of tastes are satisfied. Meanwhile, tasteless tobacco tar can also be stored in one tobacco tar bin, namely it is only used for providing the smoke, a tobacco tar extracting solution is stored in another tobacco tar bin, namely it is used for providing smoke with flavor, and then the two kinds of smoke are mixed, therefore the amount of smoke can be increased, and the flavor of the true cigarette can also be simulated.

Further, a first sealing cover is arranged between the atomization core and an inner side wall of the branch pipe, and a third gas pass hole which communicates the second gas pass hole and the suction nozzle is formed in the first sealing cover.

The first sealing cover ensures good sealing property between the atomization core and the branch pipe so as to prevent the leakage of the tobacco tar.

As a preferred implementation, a bottom cover is connected to one end, away from the suction nozzle, of the side wall of the tobacco tar cup, one end, away from the branch pipe, of the atomization core is fixedly connected with the bottom cover, a through hole communicated with the first gas pass hole is formed in the bottom cover, a second sealing cover is arranged between the atomization core and an inner side wall of the bottom cover, and a fourth gas pass hole communicated with the first gas pass hole is formed in the second sealing cover; and the gas enters from the through hole and is divided into three paths after passing through the fourth gas pass hole and the first gas pass hole, the first path outflows from the second gas pass hole after flowing by the first surface, the second path outflows from the second gas pass hole after flowing through the solid tobacco product, and the third path outflows from the second gas pass hole after flowing by the fourth surface.

The second sealing cover ensures good sealing property between the atomization core and the bottom cover so as to prevent the leakage of the tobacco tar.

As another preferred implementation, a hollow cavity communicated with the outside is arranged between the inner side wall of the branch pipe and the outer side wall of the smoke mixing pipe, and both of the first atomization sheet and the second atomization sheet prop against the smoke mixing pipe; the hollow cavity is communicated with the solid tobacco product by the first surface; the hollow cavity is further communicated with the solid tobacco product by the fourth surface; and the gas is divided into two paths after entering the hollow cavity, the first path outflows from the second gas pass hole after flowing by the first surface and flowing through the solid tobacco product successively, and the second path outflows from the second gas pass hole after flowing by the fourth surface and flowing through the solid tobacco product successively.

By means of the above structure, the gas enters from the atomization surface which atomize tobacco tar, and then is discharged from the space between the two atomization sheets, so that the smoke is mixed more uniformly; meanwhile the solid tobacco product can also filter or re-atomize the large-granule smoke produced by the tobacco tar again, so that the taste of the smoke finally obtained is better and smoother.

As a preferred implementation, the atomization core is detachably connected with the division plate.

Further, the smoke mixing pipe is provided with internal threads.

As the smoke mixing pipe is provided with the internal threads, the smoke can helically flow in the smoke mixing pipe, therefore the smoke is mixed more uniformly, and the user experience is improved.

Compared with the prior art, the ultrasonic electronic cigarette atomization core of the utility model not only can atomize two kinds of tobacco tar at the same time, but also can atomize the solid tobacco product, and the amount of smoke is large, therefore the demands of smokers for different tastes, in particular the demands for the taste of true cigarette, can be satisfied.

Figure 1:
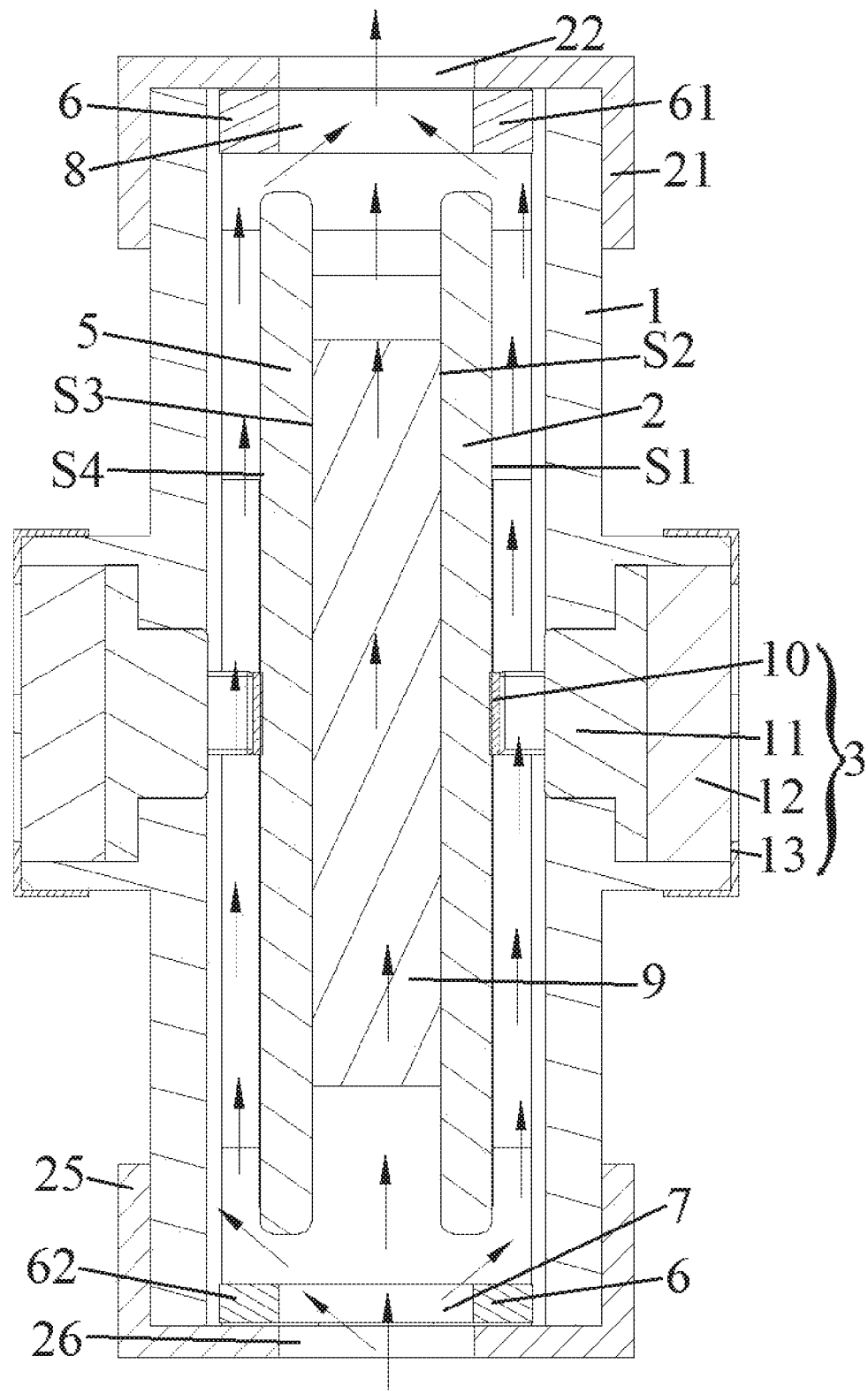
FIG. 1 is a front section view of the atomization core of embodiment 1.
Figure 2:
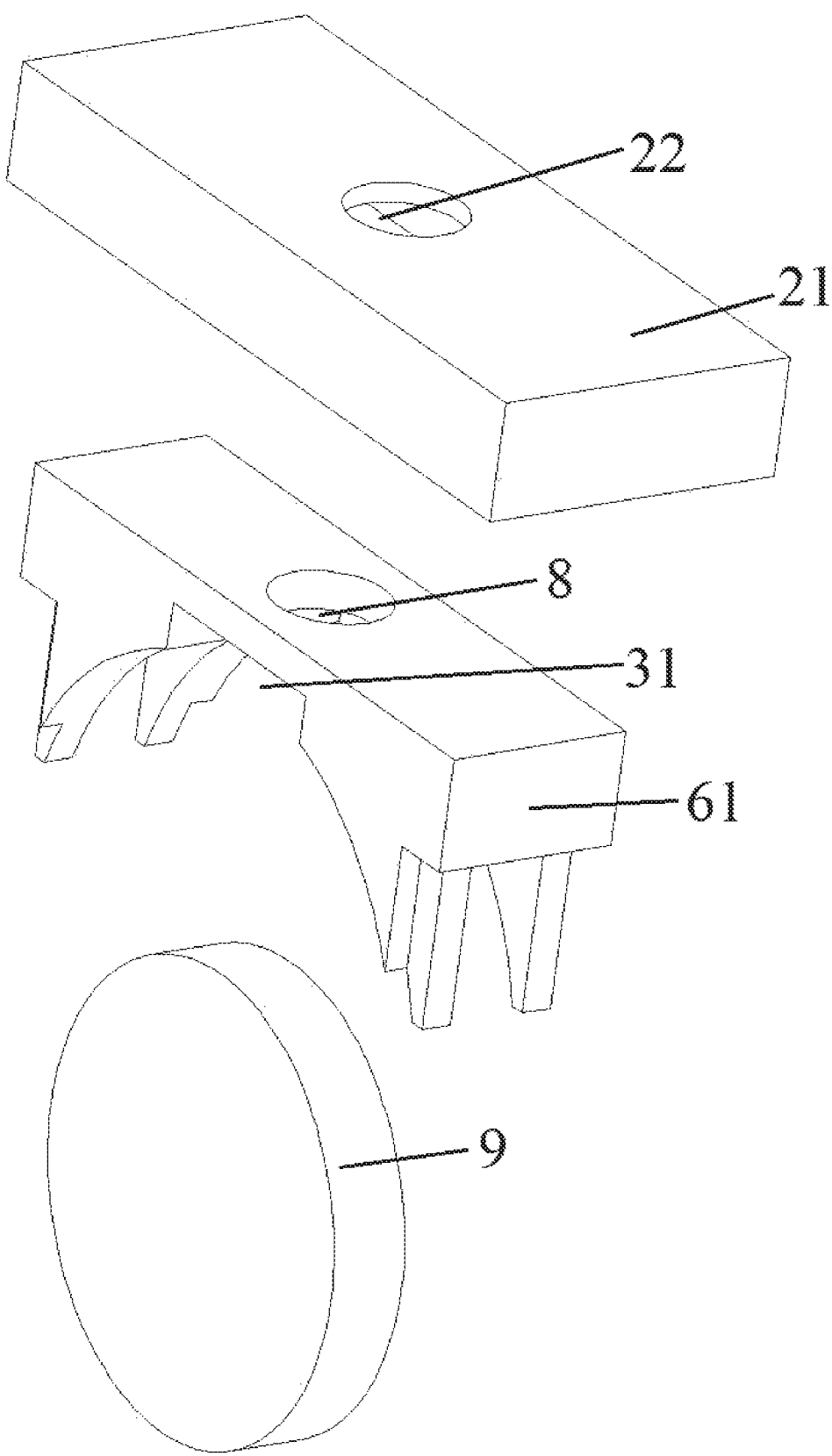
FIG. 2, FIG. 3 and FIG. 4 constitute an exploded view of FIG. 1.
Figure 3:
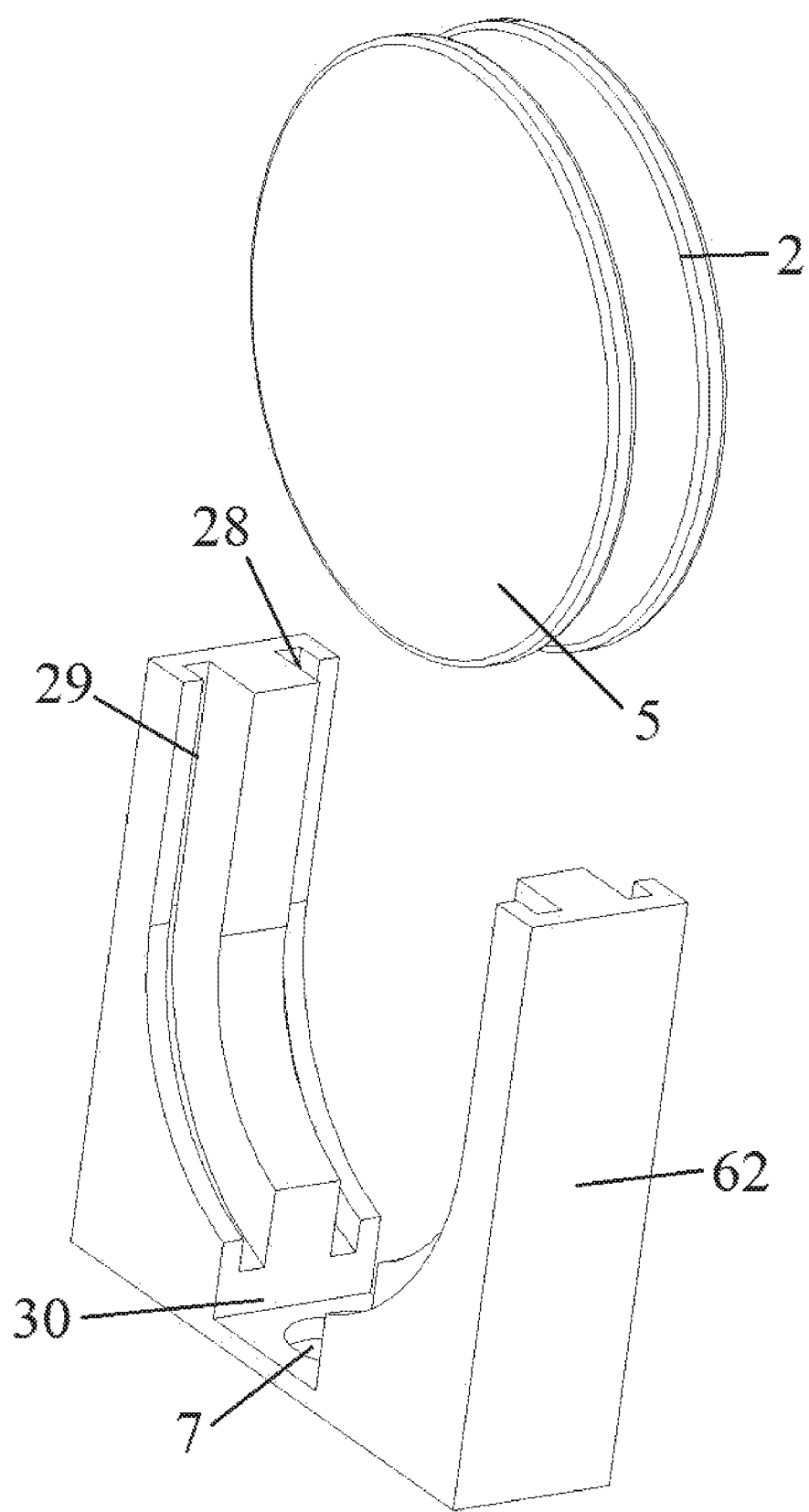
Figure 4:
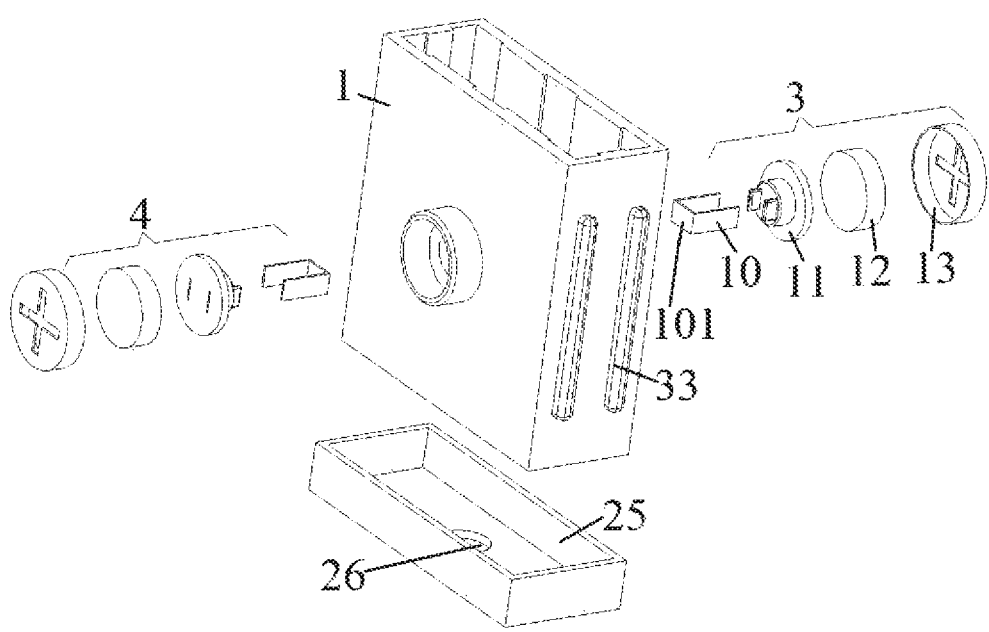

Reference signs: 1—atomization core fixing sleeve, 2—first atomization sheet, S1—first surface, S2—second surface, 3—first tobacco tar guide component, 4—second tobacco tar guide component, 5—second atomization sheet, S3—third surface, S4—fourth surface, 6—bracket, 61—upper bracket, 62—lower bracket, 7—first gas pass hole, 8—second gas pass hole, 9—solid tobacco product, 10—tobacco tar guide cotton, 101—atomization cotton, 11—fixing ring, 12—tobacco tar storage cotton, 13—tobacco tar control cover, 14—tobacco tar cup, 15—suction nozzle, 16—division plate, 17—branch pipe, 18—first tobacco tar bin, 19—second tobacco tar bin, 20—smoke mixing pipe, 21—first sealing cover, 22—third gas pass hole, 23—bottom cover, 24—through hole, 25—second sealing cover, 26—fourth gas pass hole, 27—hollow cavity, 28—first clamping slot, 29—second clamping slot, 30—first through groove, 31—second through groove, 32—guide groove, 33—guide strip, 34—upper cover, 35—sealing ring, 36—first tobacco tar injection hole, 37—second tobacco tar injection hole, 38—first tobacco tar injection plug, 39—second tobacco tar injection plug, 40—connecting seat, 41—inner electrode, 42—insulating ring, 43—first gas inlet hole, 44—second gas inlet hole, 45—third gas inlet hole.

SPECIFIC MODE FOR CARRYING OUT THE INVENTION

Embodiment 1

As shown in FIG. 1 to FIG. 4, an atomization core of embodiment 1 of the utility model comprises an atomization core fixing sleeve 1, wherein a first atomization sheet 2, a first tobacco tar guide component 3 and a bracket 6 are arranged in the atomization core fixing sleeve 1, the first atomization sheet 2 comprises a first surface S1 and a second surface S2, the first atomization sheet 2 is fixed on the bracket 6, and the first tobacco tar guide component 3 props against the first surface S1; a second atomization sheet 5 and a second tobacco tar guide component 4 are further arranged in the atomization core fixing sleeve 1, the second atomization sheet 5 comprises a third surface S3 and a fourth surface S4, the second atomization sheet 5 is fixed on the bracket 6, and the second tobacco tar guide component 4 props against the fourth surface S4; both a first gas pass hole 7 and a second gas pass hole 8 are formed in the bracket 6 and are communicated with the outside, both of the first gas pass hole 7 and the second gas pass hole 8 are communicated with the first surface S1, and both of the first gas pass hole 7 and the second gas pass hole 8 are communicated with the fourth surface S4.

Both of the first atomization sheet 2 and the second atomization sheet 5 are solid piezoelectric ceramic pieces.

The second surface S2 and the third surface S3 are arranged oppositely, and a solid tobacco product 9 is clamped between the second surface S2 and the third surface S3; and both of the first gas pass hole 7 and the second gas pass hole 8 are communicated with the solid tobacco product 9.

The bracket 6 comprises an upper bracket 61 and a lower bracket 62 that are detachably connected, a first clamping slot 28 which clamps and fixes the first atomization sheet 2 and a second clamping slot 29 which clamps and fixes the second atomization sheet 5 are formed in an inner side wall of the lower bracket 62. The first atomization sheet 2 and the second atomization sheet 5 are installed in the lower bracket 62, then the solid tobacco product 9 is received between the first atomization sheet 2 and the second atomization sheet 5, and the upper bracket 61 is put thereon, therefore the assembly is simple.

A first through groove 30 communicated with the first gas pass hole 7 is formed in the lower bracket 62, a second through groove 31 communicated with the second gas pass hole 8 is formed in the upper bracket 61, the first through groove 30 is mainly used for communicating atomization surfaces on the first atomization sheet 2 and the second atomization sheet 5, so that the gas entering the bracket 6 respectively flows through each atomization sheet to take away the smoke or flavor, and the second through groove 31 is used for collecting the smoke or flavor produced by the atomization of each atomization surface into the second gas pass hole 8 and discharging the smoke or flavor to be inhaled by the user. The direction indicated by an arrow in FIG. 1 is a gas flow direction.

The first tobacco tar guide component 3 comprises tobacco tar guide cotton 10, a fixing ring 11, tobacco tar storage cotton 12 and a tobacco tar control cover 13, the tobacco tar guide cotton 10 is a U-shaped structure which is formed by two opposite side walls and atomization cotton 101, the two side walls of the tobacco tar guide cotton 10 penetrate through the fixing ring 11 and are in contact with one side face of the tobacco tar storage cotton 12, and the other side face of the tobacco tar storage cotton 12 is in contact with one side of the tobacco tar control cover 13; and one side of the atomization cotton 101 is in contact with the first surface S1. As shown in the drawings, the contact area between the atomization cotton 101 and the first atomization sheet 2 is relatively small, therefore the atomization start up time is short, and the user experience is improved.

The structure of the second tobacco tar guide component 4 is the same as that of the first tobacco tar guide component 3.

As shown in FIG. 5 to FIG. 11, an atomizer of embodiment 1 of the utility model comprises a tobacco tar cup 14 and a suction nozzle 15 connected with one end of the side wall of the tobacco tar cup 14, the ultrasonic electronic cigarette atomization core of embodiment 1 is arranged in the tobacco tar cup 14, a division plate 16 is arranged in the tobacco tar cup 14, and a branch pipe 17 is arranged in the side wall of the division plate 16; the division plate 16 and the atomization core divide the tobacco tar cup 14 into a first tobacco tar bin 18 and a second tobacco tar bin 19 which are not communicated with each other, the first tobacco tar bin 18 is communicated with the first surface S1 through the first tobacco tar guide component 3, and the second tobacco tar bin 19 is communicated with the fourth surface S4 through the second tobacco tar guide component 4; and a smoke mixing pipe 20 is arranged in the branch pipe 17, and the second gas pass hole 8 is communicated with the suction nozzle 15 through the smoke mixing pipe 20. A working power supply for supplying power to the first atomization sheet 2 and the second atomization sheet 5 is further arranged in the atomizer and is not shown in the drawings.

A first sealing cover 21 is arranged between the atomization core and an inner side wall of the branch pipe 17, and a third gas pass hole 22 which communicates the second gas pass hole 8 and the suction nozzle 15 is formed in the first sealing cover 21.

A bottom cover 23 is connected to one end, away from the suction nozzle 15, of the side wall of the tobacco tar cup, one end, away from the branch pipe 17, of the atomization core is fixedly connected with the bottom cover 23, a through hole 24 communicated with the first gas pass hole 7 is formed in the bottom cover 23, a second sealing cover 25 is arranged between the atomization core and the inner side wall of the bottom cover 23, and a fourth gas pass hole 26 communicated with the first gas pass hole 7 is formed in the second sealing cover 25; and the gas enters from the through hole 24 and is divided into three paths after passing through the fourth gas pass hole 26 and the first gas pass hole 7, the first path outflows from the second gas pass hole 8 after flowing by the first surface S1, the second path outflows from the second gas pass hole 8 after flowing through the solid tobacco product 9, and the third path outflows from the second gas pass hole 8 after flowing by the fourth surface S4.

Figure 5:
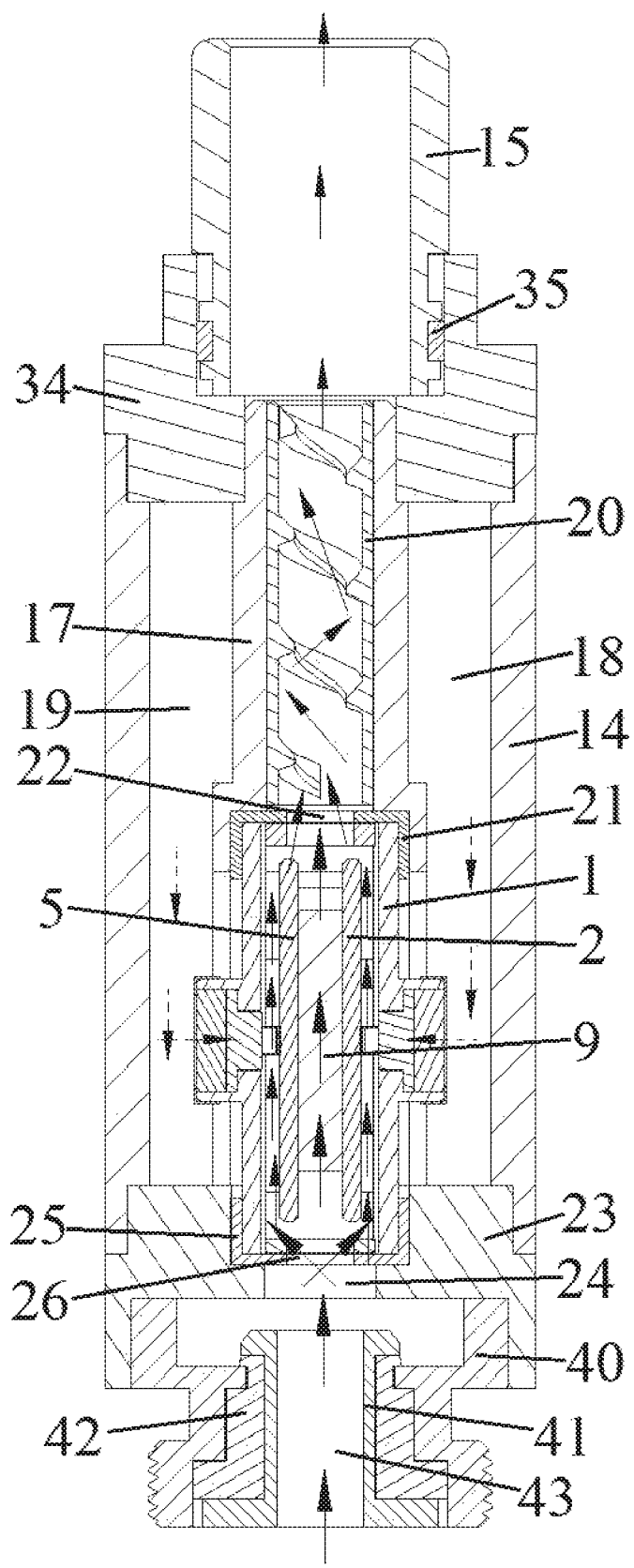
FIG. 5 is a front section view of the atomizer of embodiment 1.
Figure 6:
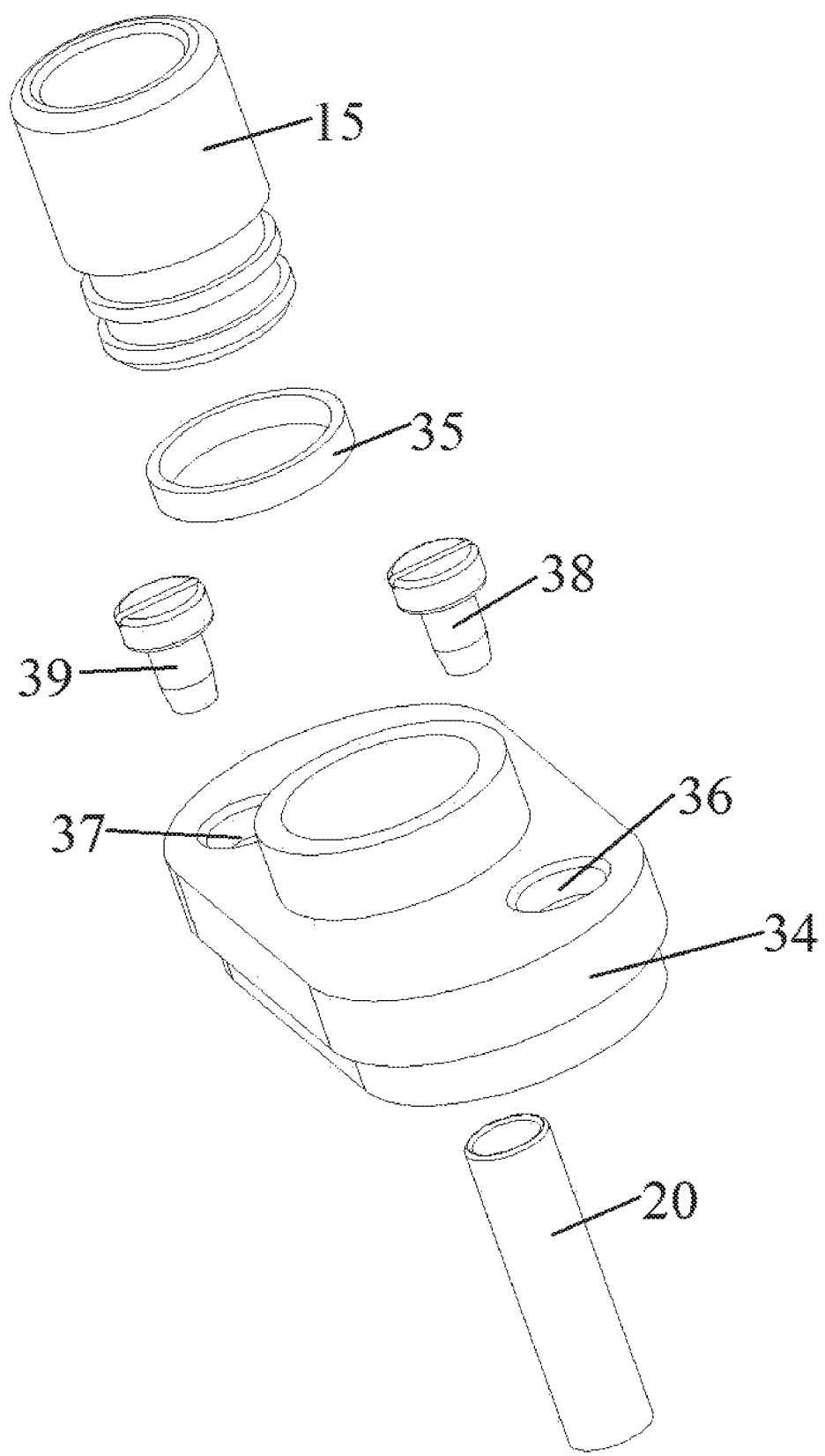
FIG. 6, FIG. 7 and FIG. 8 constitute an exploded view of FIG. 5.
Figure 7:
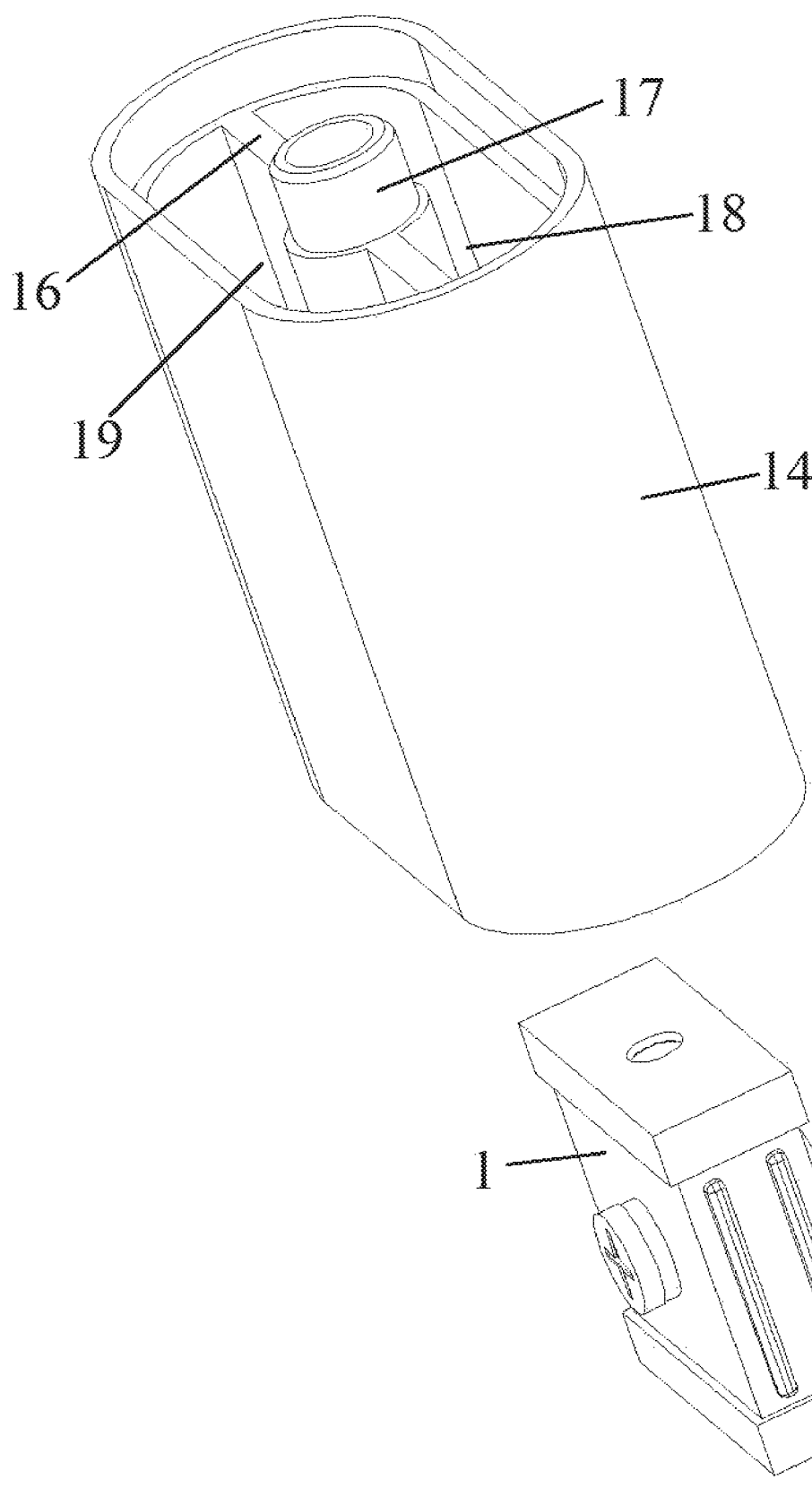
Figure 8:
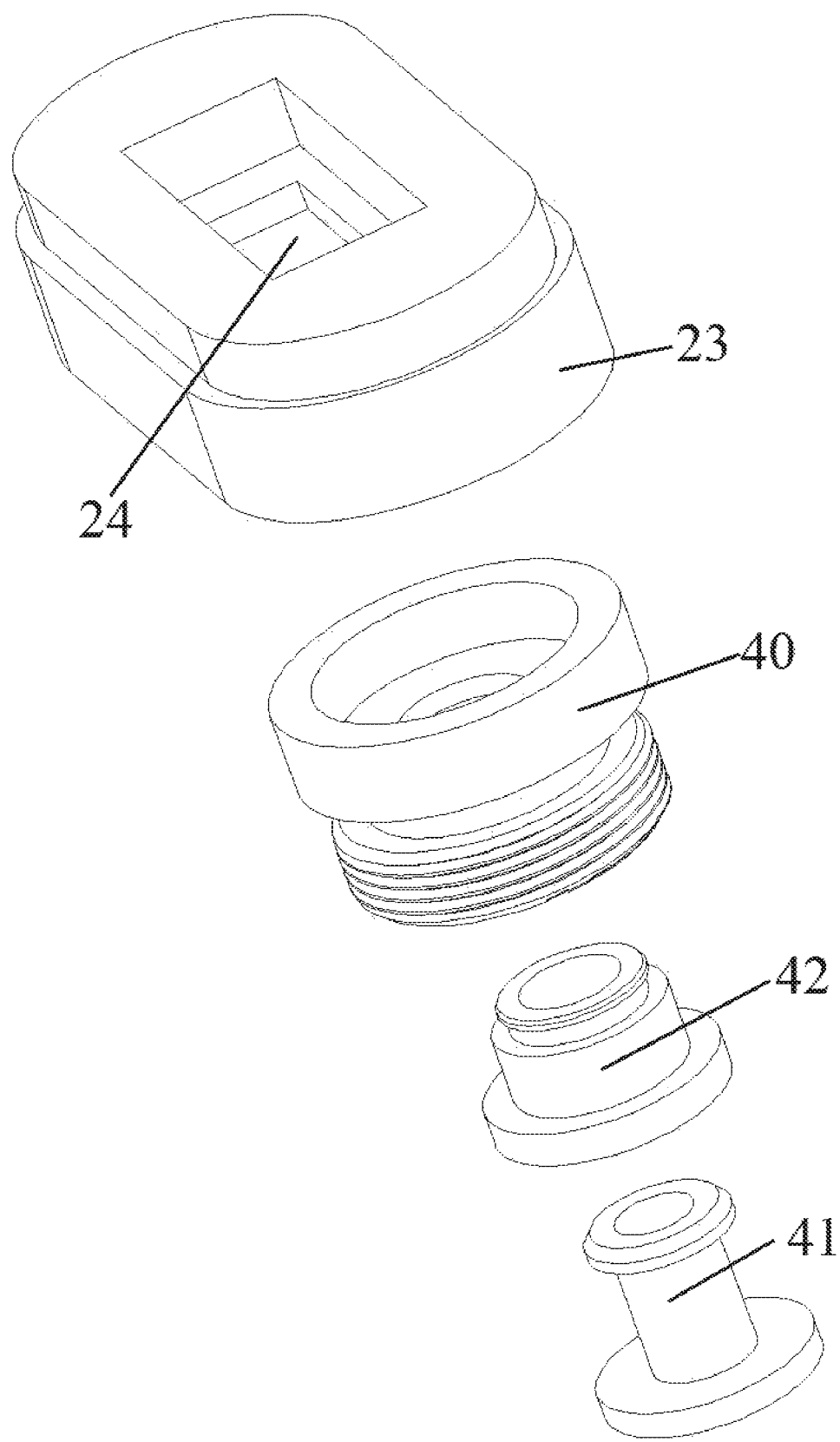
Figure 9:
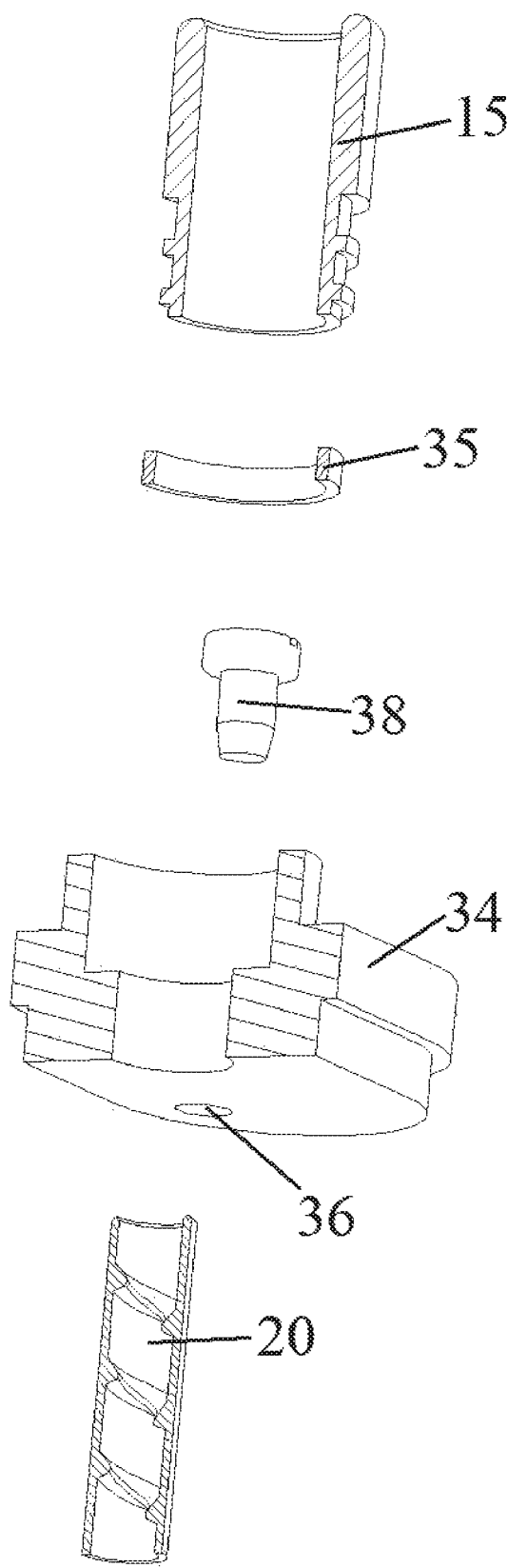
FIG. 9 is an oblique section view of FIG. 6.
Figure 10:
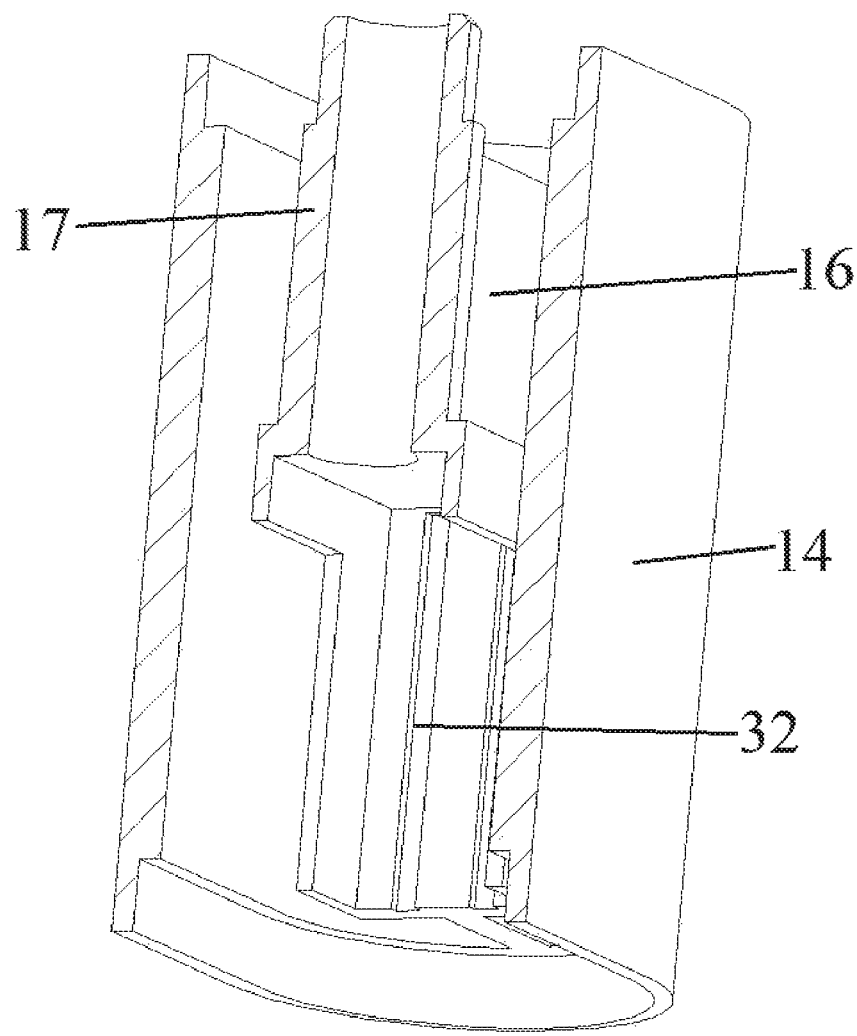
FIG. 10 is an oblique section view of FIG. 7.
Figure 10:
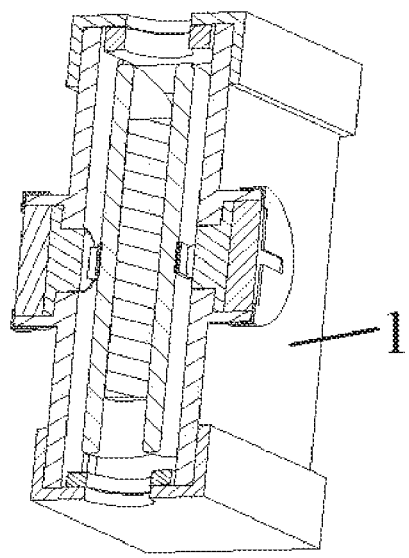
Figure 11:
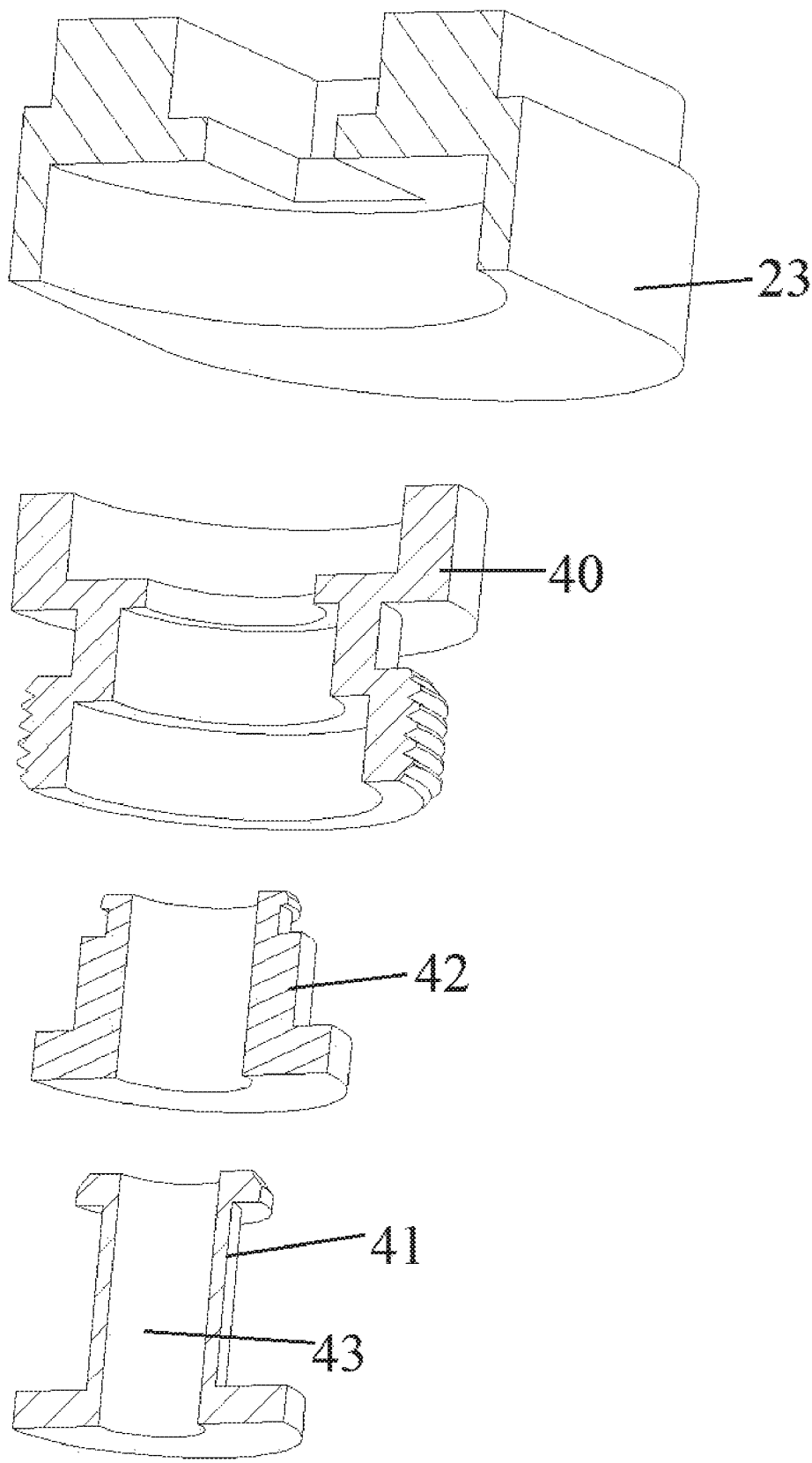
FIG. 11 is an oblique section view of FIG. 8.

The direction indicated by a dotted arrow in FIG. 5 is a tobacco tar guide direction, and the direction indicated by a solid arrow is a gas flow direction.

The atomization core is detachably connected with the division plate 16. Both of the first surface S1 and the division plate 16 are parallel to the length direction of the electronic cigarette, a cavity which accommodates the atomization core is formed in the division plate 16, a guide groove 32 parallel to the length direction of the electronic cigarette is formed in the side wall of the cavity, and guide strips 33 corresponding to the guide groove 32 are arranged on the atomization core fixing sleeve 1.

The smoke mixing pipe 20 is provided with internal threads.

The suction nozzle 15 is connected with the tobacco tar cup 14 through an upper cover 34. A sealing ring 35 is arranged between the suction nozzle 15 and the upper cover 34. A first tobacco tar injection hole 36 communicated with the first tobacco tar bin 18 and a second tobacco tar injection hole 37 communicated with the second tobacco tar bin 19 are formed in the upper cover 34, the first tobacco tar injection hole 36 is provided with a first tobacco tar injection plug 38, and the second tobacco tar injection hole 37 is provided with a second tobacco tar injection plug 39.

One side, away from the atomization core, of the bottom cover 23 is fixedly connected with a connecting seat 40, an inner electrode 41 is fixed at the bottom of the connecting seat 40 through an insulating ring 42, a first gas inlet hole 43 is formed in the inner electrode 41, and the first gas inlet hole 43 is communicated with the fourth gas pass hole 26 through the through hole 24. As shown in FIG. 5, the gas enters from the first gas inlet hole 43, enters the bracket 6 after passing through the through hole 24, the fourth gas pass hole 26 and the first gas pass hole 7 successively to be divided into three paths, the first path flows to the second gas pass hole 8 after flowing by the first surface S1, the second path flows to the second gas pass hole 8 after flowing through the solid tobacco product 9, the third path flows to the second gas pass hole 8 after flowing by the fourth surface S4, the three kinds of smoke are mixed at the second gas pass hole 8, enter the smoke mixing pipe 20 through the third gas pass hole 22, and are mixed in the smoke mixing pipe 20 and finally enter the mouth of the user from the suction nozzle 15.

Embodiment 2

Figure 12:
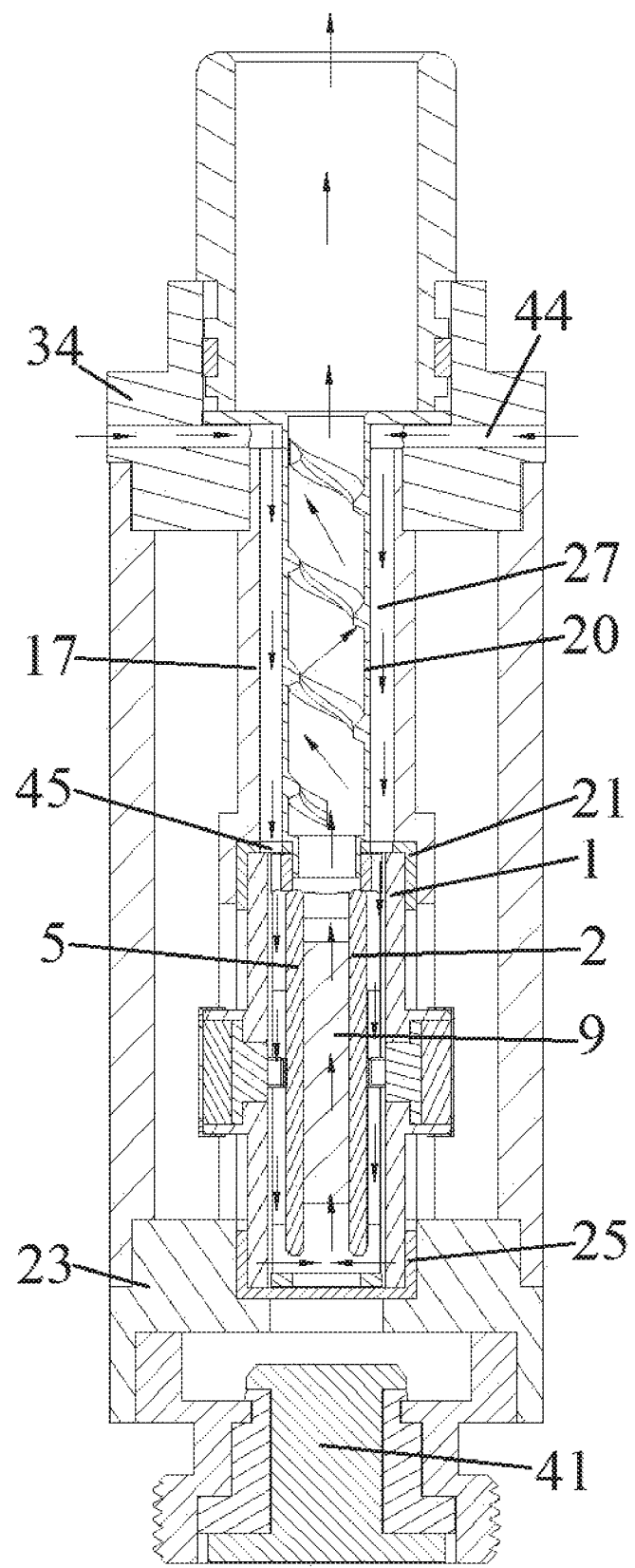
FIG. 12 is a front section view of the atomizer of embodiment 2.
Figure 13:
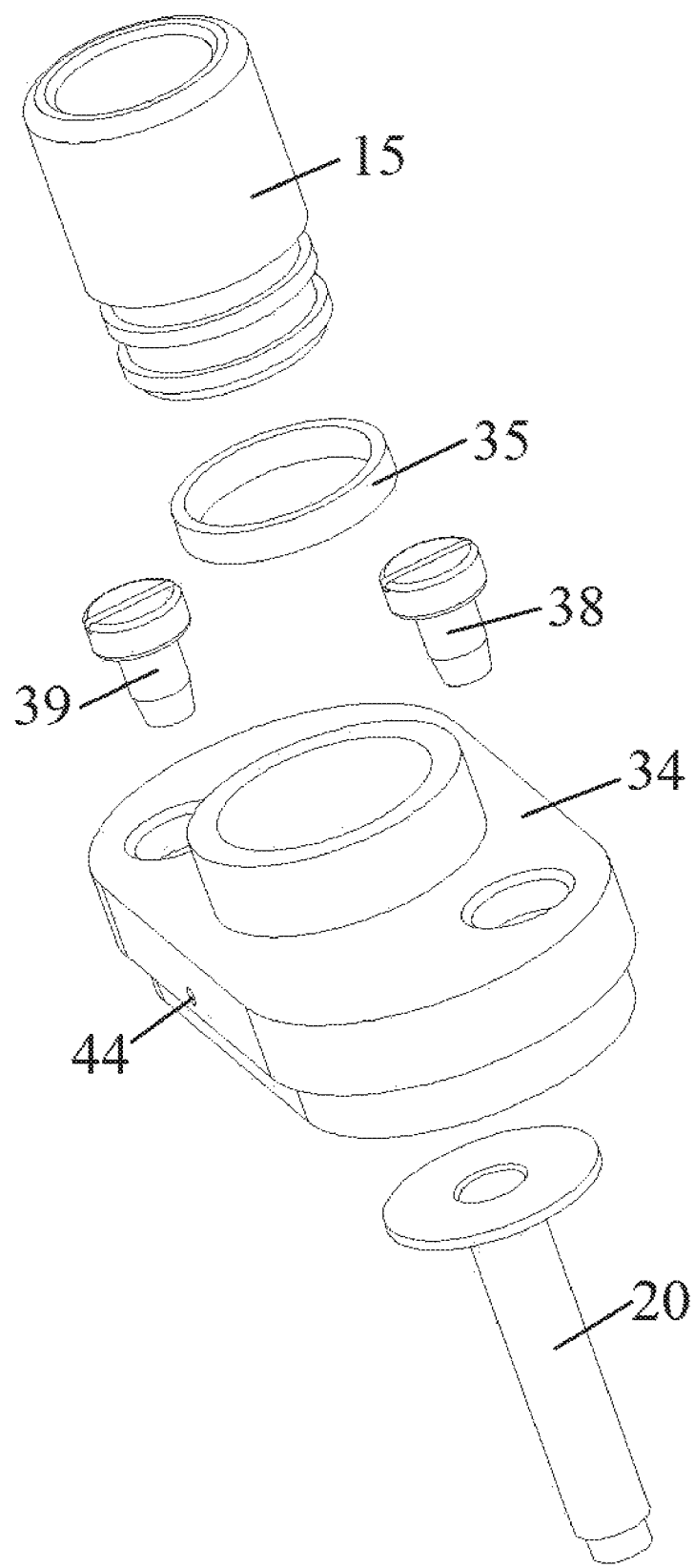
FIG. 13, FIG. 14 and FIG. 15 constitute an exploded view of FIG. 12.
Figure 14:
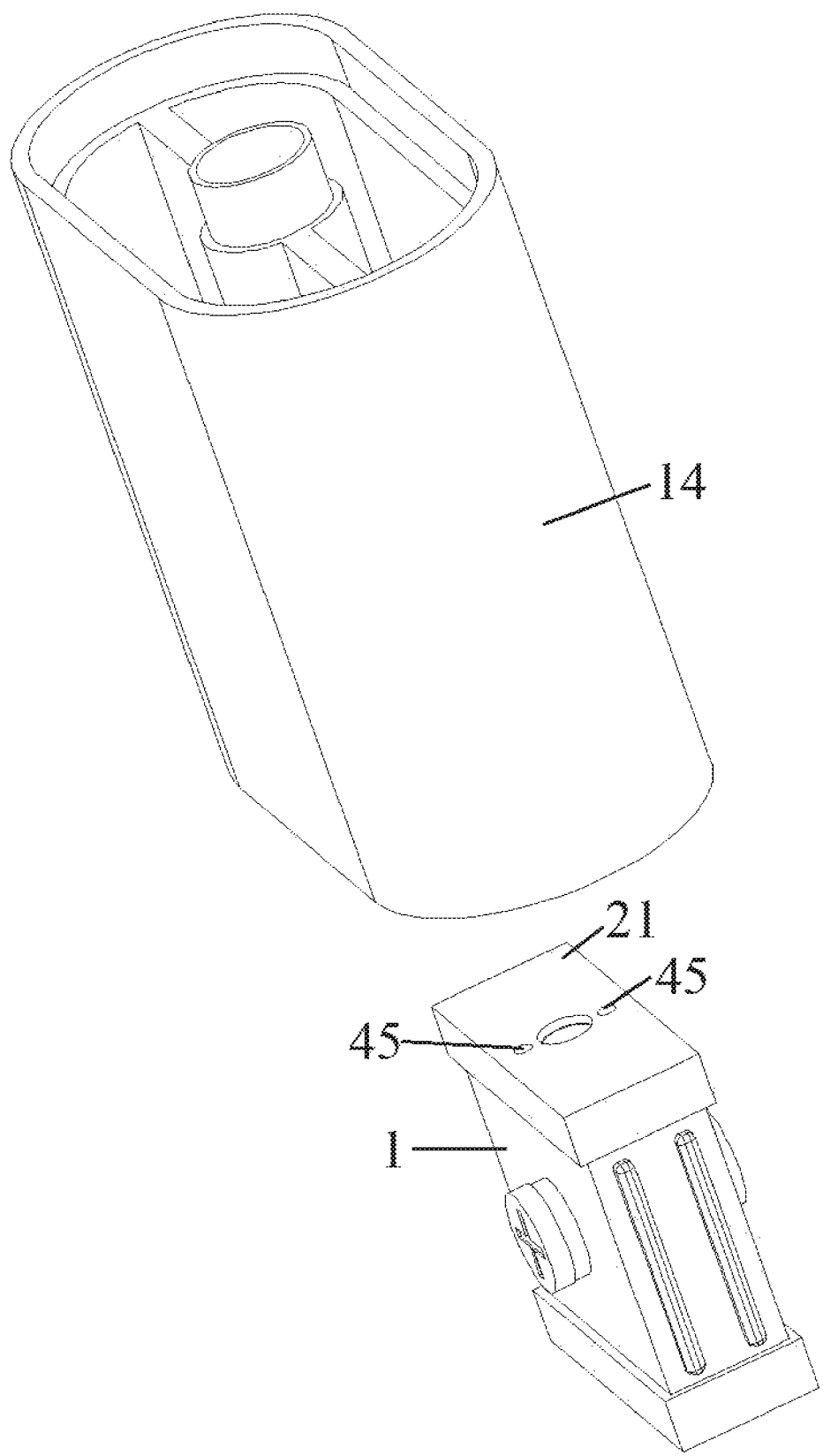
Figure 15:
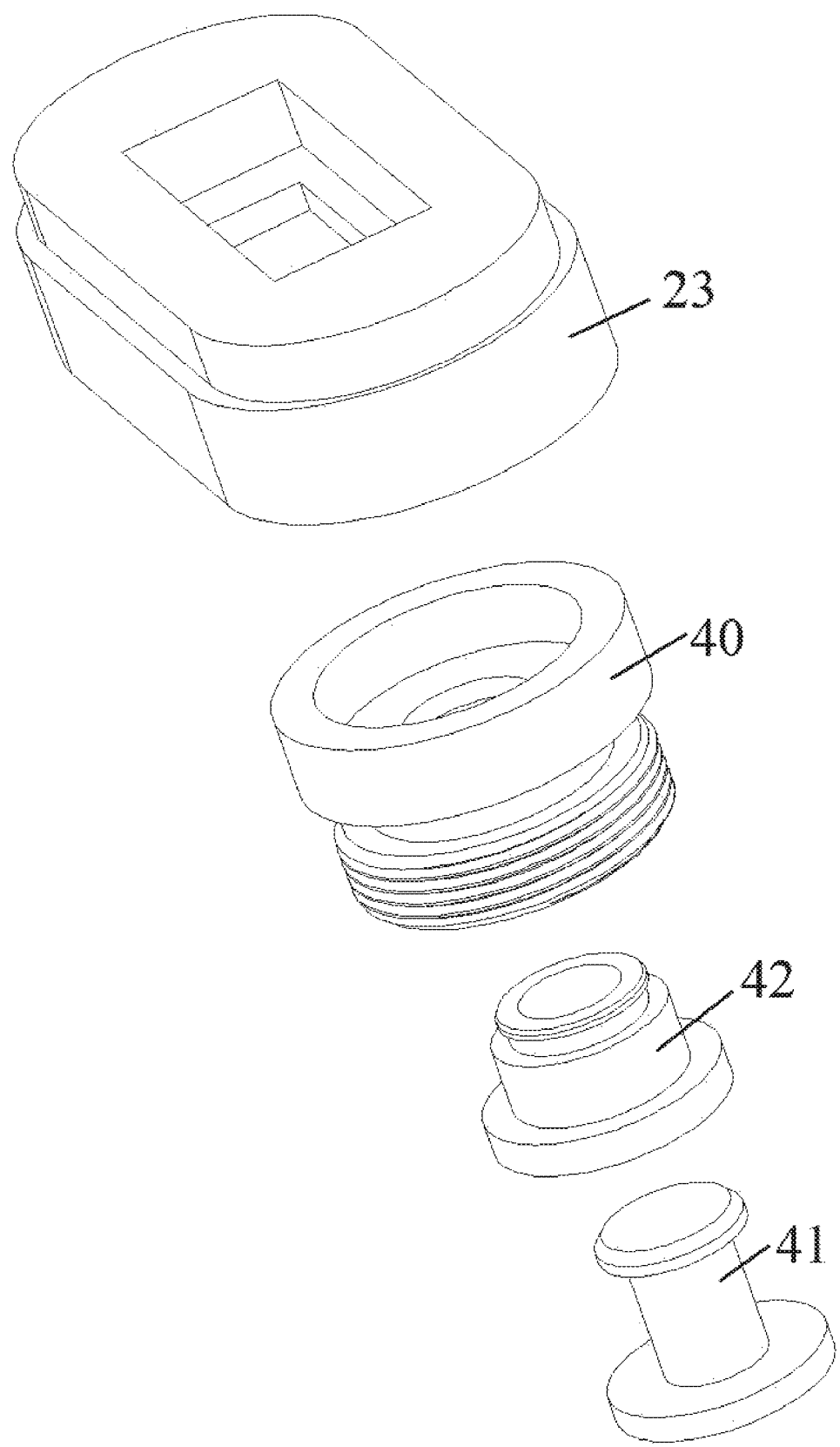
Figure 16:
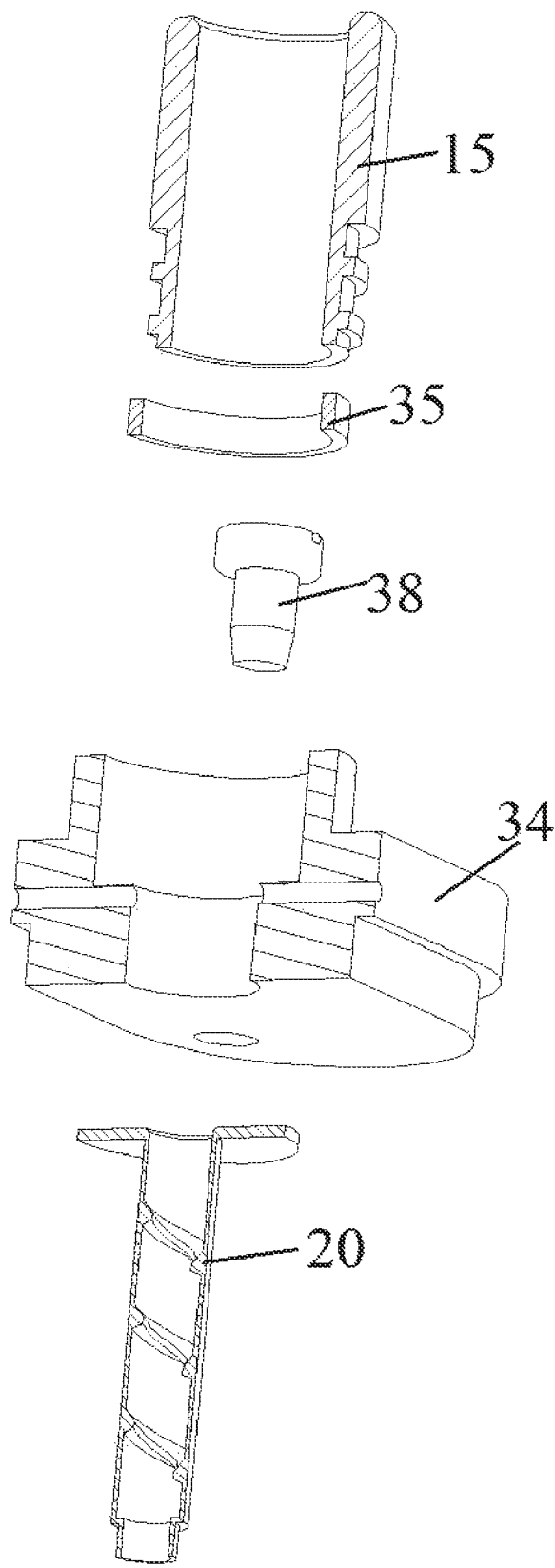
FIG. 16 is an oblique section view of FIG. 13.
Figure 17:
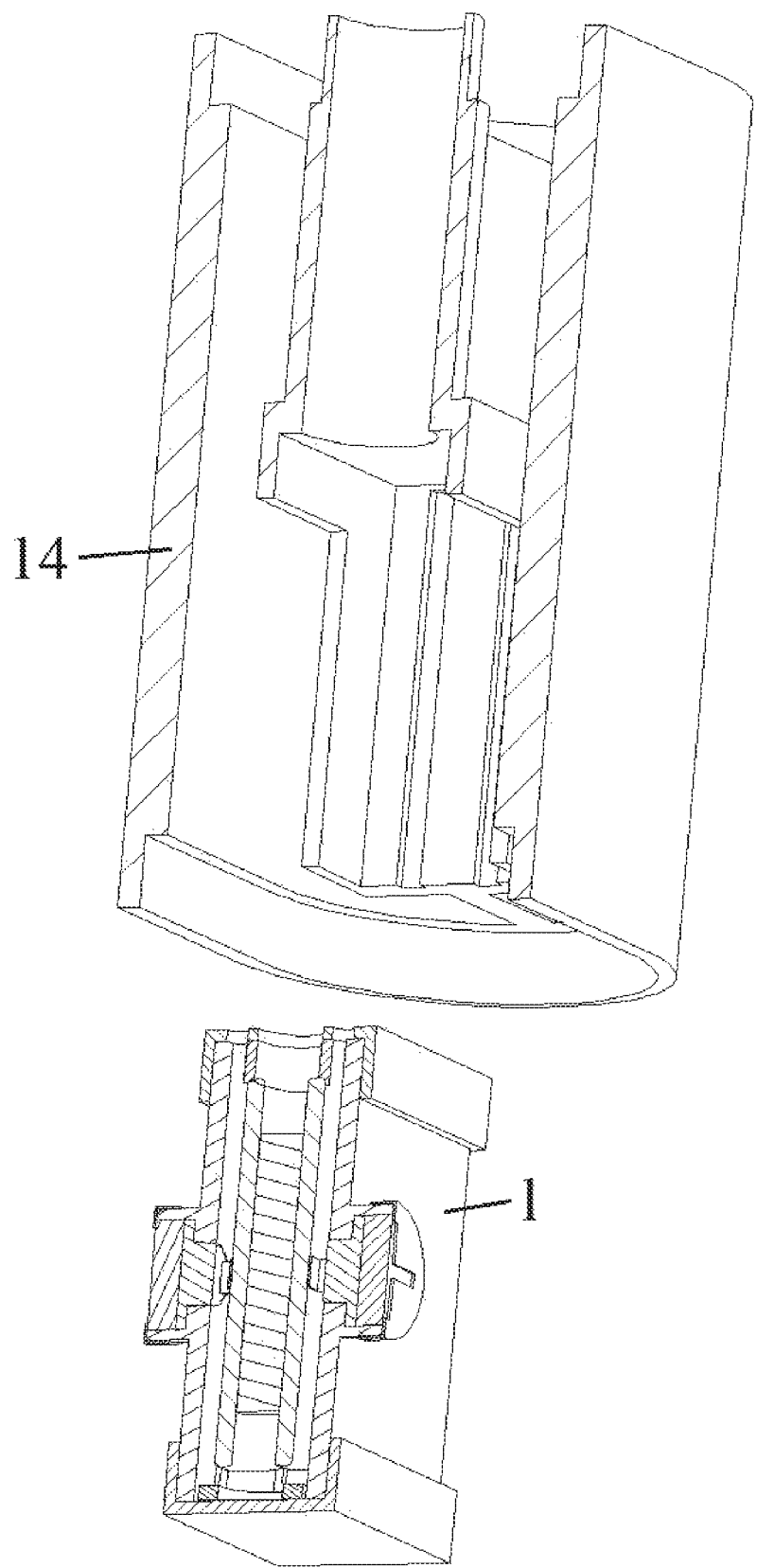
FIG. 17 is an oblique section view of FIG. 14.
Figure 18:
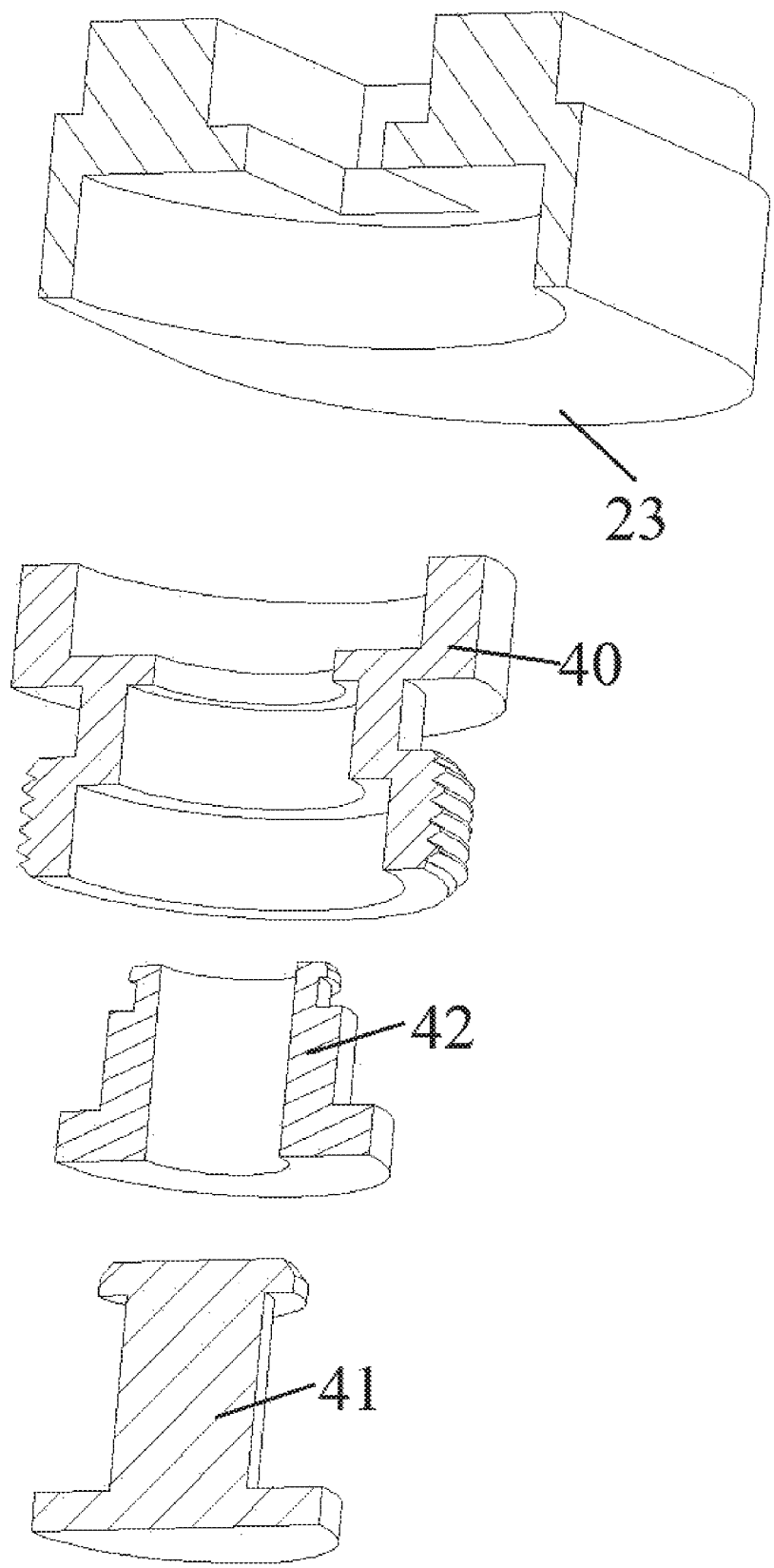
FIG. 18 is an oblique section view of FIG. 15.

FIG. 12 to FIG. 18 show the structure of atomization core and the atomizer of embodiment 2 of the utility model, and the structure in embodiment 2 is similar to the structure in embodiment 1. The difference lies in that the airflow direction is different. The first gas inlet hole 43 in embodiment 1 is not formed in the inner electrode 41 in embodiment 2, and meanwhile, the fourth gas pass hole 26 in embodiment 1 is not formed in the second sealing cover 25 in embodiment 2 as well. In embodiment 2, a second gas inlet hole 44 is formed in the upper cover 34, a third gas inlet hole 45 is formed in the first sealing cover 21, a hollow cavity 27 communicated with the outside through the second gas inlet hole 44 is arranged between the inner side wall of the branch pipe 17 and the outer side wall of the smoke mixing pipe 20, and both of the first atomization sheet 2 and the second atomization sheet 5 prop against the smoke mixing pipe 20; and the hollow cavity 27 is communicated with the solid tobacco product 9 by the first surface S1, and the hollow cavity 27 is further communicated with the solid tobacco product 9 by the fourth surface S4, The direction indicated by the arrow in FIG. 12 is the airflow direction, as shown in FIG. 12, the gas enters the atomization core fixing sleeve 1 after flowing through the second gas inlet hole 44, the hollow cavity 27 and the third gas inlet hole 45 successively and is divided into two paths, the first path flows to the second gas pass hole 8 after flowing by the first surface S1 and flowing through the solid tobacco product 9 successively, the second path flows to the second gas pass hole 8 after flowing by the fourth surface S4 and flowing through the solid tobacco product 9 successively, and the mixed smoke enters the mouth of the user through the third gas pass hole 22, the smoke mixing pipe 20 and the suction nozzle 15.

The structure in embodiment 2 same as that in embodiment 1 is not repeated redundantly herein, but it does not affect how those skilled in the art understand and implement the utility model.

Although the embodiments of the utility model have been described above in combination with the drawings, the utility model is not limited to the specific embodiments described above, and the specific embodiments described above are merely illustrative and are not restrictive, those of ordinary people skilled in the art can also make a lot of forms under the enlightenment of the utility model without departing from the purpose of the utility model or the protection scope of the claims, and all these forms fall within the protection scope of the utility model.

The invention claimed is:

1. An ultrasonic electronic cigarette atomization core, comprising an atomization core fixing sleeve,
    wherein a first atomization sheet, a first tobacco tar guide component and a bracket are arranged in the atomization core fixing sleeve,
    wherein the first atomization sheet comprises a first surface and a second surface, the first atomization sheet is fixed on the bracket, and the first tobacco tar guide component props against the first surface,
    wherein a second atomization sheet and a second tobacco tar guide component are further arranged in the atomization core fixing sleeve,
    wherein the second atomization sheet comprises a third surface and a fourth surface, the second atomization sheet is fixed on the bracket, and the second tobacco tar guide component props against the fourth surface,
    wherein both a first gas pass hole and a second gas pass hole are formed in the bracket and are fluidly communicated with an outside of the electronic cigarette, both of the first gas pass hole and the second gas pass hole are fluidly communicated with the first surface, and both of the first gas pass hole and the second gas pass hole are fluidly communicated with the fourth surface,
    wherein the second surface and the third surface are arranged oppositely, a solid tobacco product is clamped between the second surface and the third surface, and both of the first gas pass hole and the second gas pass hole are fluidly communicated with the solid tobacco product.

2. The ultrasonic electronic cigarette atomization core of claim 1,
    wherein the first tobacco tar guide component comprises tobacco tar guide cotton, a fixing ring, tobacco tar storage cotton and a tobacco tar control cover,
    wherein the tobacco tar guide cotton is a U-shaped structure which is formed by two opposite side walls and atomization cotton, the two side walls of the tobacco tar guide cotton penetrate through the fixing ring and are in contact with one side face of the tobacco tar storage cotton, and an other side face of the tobacco tar storage cotton is in contact with one side of the tobacco tar control cover, and one side of the atomization cotton is in contact with the first surface.

3. The ultrasonic electronic cigarette atomization core of claim 1, wherein a structure of the second tobacco tar guide component is the same as that of the first tobacco tar guide component.

4. An ultrasonic electronic cigarette atomizer, comprising a tobacco tar cup and a suction nozzle connected with one end of a side wall of the tobacco tar cup,
wherein the ultrasonic electronic cigarette atomization core of claim 1 is arranged in the tobacco tar cup, a division plate is arranged in the tobacco tar cup, and a branch pipe is arranged in a side wall of the division plate,
wherein the division plate and the atomization core divide the tobacco tar cup into a first tobacco tar bin and a second tobacco tar bin which are not fluidly communicated with each other, the first tobacco tar bin is fluidly communicated with the first surface through the first tobacco tar guide component, and the second tobacco tar bin is fluidly communicated with the fourth surface through the second tobacco tar guide component, and a smoke mixing pipe is arranged in the branch pipe, and the second gas pass hole is fluidly communicated with the suction nozzle through the smoke mixing pipe.

5. The ultrasonic electronic cigarette atomizer of claim 4, wherein a first sealing cover is arranged between the atomization core and an inner side wall of the branch pipe, and a third gas pass hole which communicates the second gas pass hole and the suction nozzle is formed in the first sealing cover.

6. The ultrasonic electronic cigarette atomizer of claim 4, wherein a bottom cover is connected to one end, away from the suction nozzle, of the side wall of the tobacco tar cup, one end, away from the branch pipe, of the atomization core is fixedly connected with the bottom cover, a through hole fluidly communicated with the first gas pass hole is formed in the bottom cover, a second sealing cover is arranged between the atomization core and an inner side wall of the bottom cover, and a fourth gas pass hole fluidly communicated with the first gas pass hole is formed in the second sealing cover, and
wherein gas enters from the through hole and is divided into three paths after passing through the fourth gas pass hole and the first gas pass hole, a first path of the three paths outflows from the second gas pass hole after flowing by the first surface, a second path of the three paths outflows from the second gas pass hole after flowing through the solid tobacco product, and a third path of the three paths outflows from the second gas pass hole after flowing by the fourth surface.

7. The ultrasonic electronic cigarette atomizer of claim 4, wherein a hollow cavity fluidly communicated with the outside is arranged between an inner side wall of the branch pipe and an outer side wall of the smoke mixing pipe, and both of the first atomization sheet and the second atomization sheet prop against the smoke mixing pipe,
wherein the hollow cavity is fluidly communicated with the solid tobacco product by the first surface, wherein the hollow cavity is further fluidly communicated with the solid tobacco product by the fourth surface, and
wherein gas is divided into two paths after entering the hollow cavity, a first path of the two paths outflows from the second gas pass hole after flowing by the first surface and flowing through the solid tobacco product successively, and a second path of the two paths outflows from the second gas pass hole after flowing by the fourth surface and flowing through the solid tobacco product successively.

8. The ultrasonic electronic cigarette atomizer of claim 4, wherein the atomization core is detachably connected with the division plate.

9. The ultrasonic electronic cigarette atomizer of claim 4, wherein the smoke mixing pipe is provided with internal threads.

10. An ultrasonic electronic cigarette atomization core, comprising an atomization core fixing sleeve,
wherein a first atomization sheet, a first tobacco tar guide component and a bracket are arranged in the atomization core fixing sleeve,
wherein the first atomization sheet comprises a first surface and a second surface, the first atomization sheet is fixed on the bracket, and the first tobacco tar guide component props against the first surface,
wherein a second atomization sheet and a second tobacco tar guide component are further arranged in the atomization core fixing sleeve,
wherein the second atomization sheet comprises a third surface and a fourth surface, the second atomization sheet is fixed on the bracket, and the second tobacco tar guide component props against the fourth surface,
wherein both a first gas pass hole and a second gas pass hole are formed in the bracket and are fluidly communicated with an outside of the electronic cigarette, both of the first gas pass hole and the second gas pass hole are fluidly communicated with the first surface, and both of the first gas pass hole and the second gas pass hole are fluidly communicated with the fourth surface,
wherein the first tobacco tar guide component comprises tobacco tar guide cotton, a fixing ring, tobacco tar storage cotton and a tobacco tar control cover,
wherein the tobacco tar guide cotton is a U-shaped structure which is formed by two opposite side walls and atomization cotton, the two side walls of the tobacco tar guide cotton penetrate through the fixing ring and are in contact with one side face of the tobacco tar storage cotton, and an other side face of the tobacco tar storage cotton is in contact with one side of the tobacco tar control cover, and one side of the atomization cotton is in contact with the first surface.

11. The ultrasonic electronic cigarette atomization core of claim 10, wherein the second surface and the third surface are arranged oppositely, a solid tobacco product is clamped between the second surface and the third surface, and both of the first gas pass hole and the second gas pass hole are fluidly communicated with the solid tobacco product.

12. The ultrasonic electronic cigarette atomization core of claim 10, wherein a structure of the second tobacco tar guide component is the same as that of the first tobacco tar guide component.

* * * * *